Figure 1:
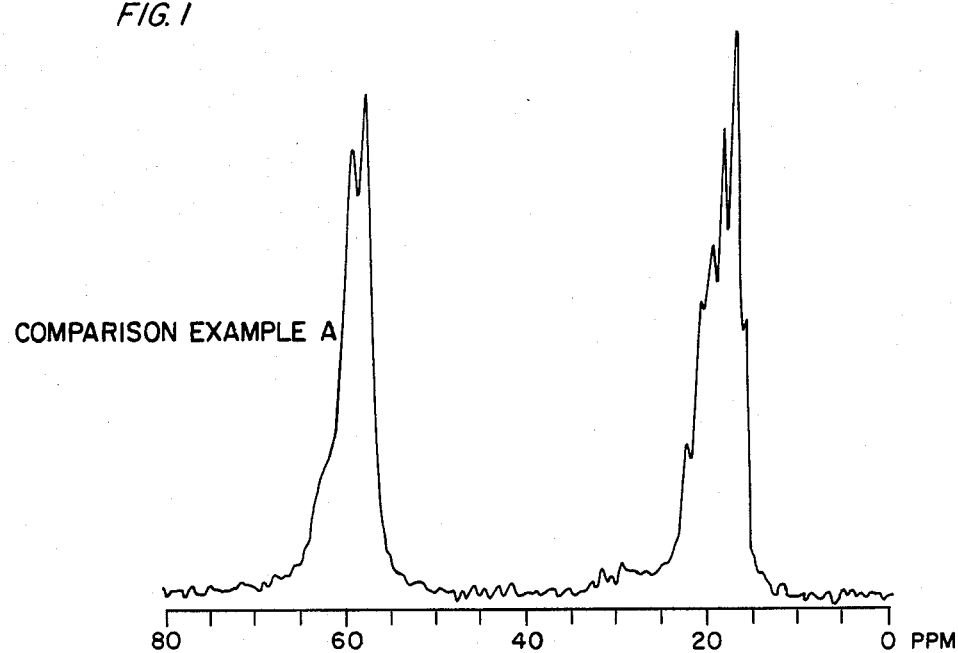
Figure 1:
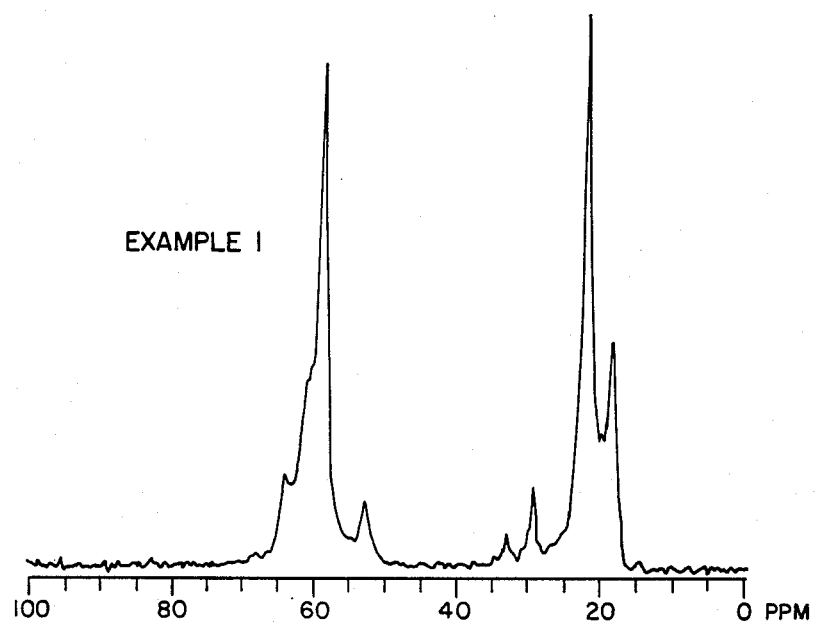

United States Patent [19]

Mehta

[11] Patent Number: 4,820,879

[45] Date of Patent: Apr. 11, 1989

[54] PREPARATION OF HYDROCARBYLOXY MAGNESIUM HALIDES

[75] Inventor: Vijay C. Mehta, Gastonia, N.C.

[73] Assignee: Lithium Corporation of America, Gastonia, N.C.

[21] Appl. No.: 58,480

[22] Filed: Jun. 5, 1987

[51] Int. Cl.[4] .................... C07C 29/70; C07C 31/28; C07C 39/02

[52] U.S. Cl. .................... 568/851; 568/652; 568/715; 568/716; 568/735; 568/807; 568/808; 568/832; 568/834; 568/838; 502/171

[58] Field of Search ............... 568/851, 716, 715, 832, 568/834, 838, 735, 807, 808, 652

[56] References Cited

U.S. PATENT DOCUMENTS

| | | | |
|---|---|---|---|
| 2,287,088 | 6/1942 | Cohen | 568/851 |
| 3,439,042 | 4/1969 | Eschnasi et al. | 260/594 |
| 3,657,361 | 4/1972 | Lenz et al. | 568/851 |
| 3,920,713 | 11/1975 | Feichtinger et al. | 260/448 |
| 4,133,824 | 1/1979 | Malpass et al. | 260/448 |
| 4,178,300 | 12/1979 | van den Berg | 260/413 |
| 4,220,554 | 9/1980 | Scata et al. | 252/429 |
| 4,370,257 | 1/1983 | Imai et al. | 568/716 |
| 4,451,688 | 5/1984 | Kuroda et al. | 585/524 |
| 4,532,361 | 7/1985 | Boden et al. | 568/851 |
| 4,681,959 | 7/1987 | Ayen et al. | 568/851 |
| 4,727,051 | 2/1988 | Breen et al. | 568/851 |

FOREIGN PATENT DOCUMENTS 57-151601 9/1982 Japan .

OTHER PUBLICATIONS

Turova and Turevskaya, Journal of Organometallic Chemistry, vol. 42, (1972), pp. 9–17.

Primary Examiner—J. E. Evans
Attorney, Agent, or Firm—Charles C. Fellows; Eugene G. Seems

[57] ABSTRACT

The present invention provides a process for making hydrocarbyloxy magnesium halides by reacting in an inert atmosphere under anhydrous conditions activated magnesium metal with an oxygen containing compound of 1 to 20 carbon atoms and an anhydrous hydrogen halide to produce a hydrocarbyloxy magnesium halide.

15 Claims, 2 Drawing Sheets

EXAMPLE 9

COMPARISON EXAMPLE C

PREPARATION OF HYDROCARBYLOXY MAGNESIUM HALIDES

This invention concerns a process for the preparation of novel hydrocarbyloxy magnesium halides and their use in making supports for the supported type Ziegler-Natta(Z/N) olefin polymerization catalyst.

Ziegler-Natta type catalysts have been employed for many years in the production of polyolefins. Many attempts have been made to obtain catalysts with higher and higher activity at high stereospecificity. Supported catalysts, particularly transition metals such as titanium supported on various carriers, very frequently a magnesium compound, have been developed. These supported catalysts greatly increase the ability of titanium and other transition metals to polymerize olefins as compared with conventional Ziegler-Natta type catalysts. Nevertheless, the ultimate catalyst has not yet been perfected.

A great deal of research has therefore gone into making supported catalysts having a magnesium compound, such as magnesium chloride, to serve as a support or carrier for titanium. R. E. Dietz in U.S. Pat. No. 4,238,354 disclosed a method for preparing a catalyst composition by mixing a milled mixture of magnesium and particulate inorganic solid selected from magnesium halides such as magnesium chloride with an alcohol to form an unagglomerated product, the alcohol being in a quantity as stoichiometrically required to convert the magnesium to a magnesium dialkoxide. This product was then contacted with titanium tetrachloride to form a catalyst from which excess titanium was washed with an inert solvent.

Masafumi Imai, et al., in U.S. Pat. No. 4,370,257 disclosed preparing magnesium containing solid product, represented by the formula ROMgX, by reacting magnesium metal, which had been preactivated by heating in a solvent, with a halogenated hydrocarbon represented by the formula RX wherein R can be an alkyl, aryl or cycloalkyl group having one to about 20 carbon atoms and X is a halogen atom, and a compound represented by the formula $X'_m C(OR')_{4-m}$ wherein $X'$ can be a hydrogen atom, a halogen atom, an alkyl, aryl, cycloalkyl group having from about one to about ten carbon atoms or a halogenated alkyl, aryl, or cycloalkyl group, R' can be an alkyl or cycloalkyl group having from about 1 to about 20 carbon atoms and M is 0, 1 or 2. Methyl iodide was used as a reaction promoter. Although many workers in this technical field considered R'OMgX could be their product few have verified the existence of such compounds.

Copending U.S. application Ser. No. 853,496 filed Apr. 18, 1986 and now abandoned discloses hydrocarbyloxy magnesium halides and a two step process for making them comprising (a) reacting activated magnesium metal with an alkyl halide and subsequently reacting this reaction product with an oxygen containing compound to produce a hydrocarbyloxy magnesium halide.

Masahiko Kuramoto in Japanese Kokai Sho 57-151601 disclosed a method of olefin polymerization using a catalyst made from the reaction product of magnesium metal, a hydrocarbon halide and an alcohol. The magnesium metal, hydrocarbon halide and alcohol were mixed together in a molar ratio of 1:0.1 to 10:0.1 to 2, respectively and reacted in heptane or hexane.

There has been much investigation into catalyst supports containing magnesium and a halide. Some investigators have made supports from magnesium alkyls, and halide containing reagents. Copending U.S. application Ser. No. 853,496 filed Apr. 18, 1986 discloses a novel process for producing organometallic hydrocarbyloxy magnesium halides some of which are low melting and/or soluble materials. This process utilizes alkyl halides as the halide source which process inherently produces an alkane as by-product. While this "alkyl halide" process produces highly desirable hydrocarbon soluble hydrocarbyloxy magnesium halide products, a lower cost process is needed.

The present invention provides a process for making organometallic hydrocarbyloxy magnesium halides which can be represented by the formula ROMgX in which RO is a hydrocarbyloxy group having 1 to 20 carbon atoms and X is a halide, preferably chloride. The process is conducted in a hydrocarbon reaction medium in an inert atmosphere. Magnesium metal, preferably iodine activated, is reacted with an oxygen containing compound containing 1 to 20 carbon atoms to produce a reaction product which is simultaneously or sequentially reacted with a dry hydrogen halide. The hydrocarbyloxy magnesium halide compound may be called a complex and as such would be considered to be a dialkoxylmagnesium compound complexed with a magnesium dihalide compound. It will be understood by those skilled in the art that these reaction products interchange very rapidly when in solution in a hydrocarbon solvent and that the formula ROMgX is employed in order to simplify disclosure and discussion of the process.

The selection of the hydrocarbon reaction medium and form of the magnesium metal largely determine whether it is advantageous to operate the present process as a one or two step process. A one step reaction can be conducted when the magnesium is in the form of chips, coarse granules, small pebble size and the like preferably activated with iodine. Such magnesium is usually activated in the reactor but can be activated separately. Typically the magnesium is charged into a reactor with crystalline iodine and refluxed for about an hour; the oxygen containing compound is then charged into the reactor and the metal containing slurry heated to reflux and reacted by the simultaneous addition of dry hydrogen halide, generally hydrogen chloride, under controlled conditions to produce the hydrocarbyloxy magnesium halide product. The one step process can be conducted using powdered or other fine particle size magnesium provided the solvent is selected from hexane, heptane, cyclohexane and other low boiling hydrocarbon solvents boiling below about 100° C.

Powdered magnesium can be used with higher boiling solvents but such reactions should be done in two steps; first the oxygen containing compound is reacted with the magnesium after which the reaction product a hydrocarbyloxy magnesium compound of the formula $(RO)_2Mg$ is reacted in a second step with a dry hydrogen halide to produce the hydrocarbyloxy magnesium halide or complex.

The reactions are conveniently conducted under anhydrous conditions using a blanket of inert gas, usually nitrogen or argon, in an inert, aprotic solvent, usually an inert hydrocarbon solvent, preferably at atmospheric pressure and reflux of the solvent but higher and lower temperatures (40° C. to 200° C.) can be used.

The term hydrocarbyloxy as used herein refers to a radical RO, a monovalent oxyhydrocarbon group such as alkoxy, cycloalkoxy, aryloxy, aralkoxy, alkenoxy and similar oxyhydrocarbon groups derived from an alkyl, cycloalkyl, alkylaryl or arylalkyl alcohol, ketone, aldehyde or ester containing 1 to 20 carbon atoms. These alcohols, ketones, aldehydes or esters are referred to herein as oxygen containing compounds. Most typically the oxygen containing compound used in this invention is a monohydric alkanol, cycloalkanol or aromatic alcohol, ROH, in which R is a hydrocarbon radical having 1–18 carbon atoms.

Unsubstituted primary monohydric alcohols or alkanols ($C_1$ to $C_{20}$), which are reacted with magnesium in various of the embodiments of this invention are exemplified by methanol, ethanol, propanol, butanol pentanol, hexyl alcohol, heptyl and higher saturated alcohols ($C_8$ to $C_{20}$).

Beta-alkyl substituted primary monohydric (normal) alcohols or alkanols ($C_5$–$C_{18}$), which are reacted with magnesium in various of the embodiments of this invention, are exemplified by 2-methyl-1-pentanol, 2-methyl-1-butanol, 2-ethyl-1-butanol, 2-ethyl-1-pentanol, 2-ethyl-1-hexanol, 2-ethyl-4-methyl-1-pentanol, 2-propyl-1-heptanol, 2-methyl-1-hexanol, 2-ethyl-5-methyl-1-octanol, 2,2-dimethyl-1-octanol, and the like, or mixtures thereof. Particularly important beta-alkyl substituted primary monohydric normal alcohols are 2-methyl-1-pentanol and 2-ethyl-1-hexanol and mixtures thereof.

Beta-alkyl substituted $C_5$–$C_{18}$ acyclic secondary alcohols; i.e., those secondary alcohols bearing at least one $C_1$–$C_4$ alkyl branch at the carbon atom beta to the hydroxyl group, which are reacted with magnesium and hydrogenhalide to make hydrocarbon soluble products of this invention exemplified by 2-methyl-3-pentanol, 2,2-dimethyl-3-pentanol, 2,4-dimethyl-3-pentanol, 3-methyl-2-pentanol, 3-methyl-2-butanol, 4-methyl-3-hexanol, 3- methyl-2-hexanol, 2,4-dimethyl-3-hexanol, 3,4-dimethyl2-hexanol, 2,4-dimethyl-3-heptanol, 4-methyl-3-heptanol 2-methyl-3-octanol, 2,2-dimethyl-3-octanol, and the like. Also contemplated are beta-alkyl substituted cyclic $C_6$–$C_{18}$ secondary alcohols such as 2-methyl-cyclopentanol, 2-methylcyclohexanol, 2,6-dimethylcyclohexanol, 2-tert-butylcyclohexanol, and the like. Most preferred are those cyclic secondary alcohols bearing at least two beta methyl groups or one beta-tert-butyl group relative to the hydroxyl moiety.

Beta-alkyl substituted $C_6$–$C_{18}$ cyclic or acyclic tertiary alcohols; i.e., those tertiary alcohols bearing at least one $C_1$–$C_4$ alkyl branch at the carbon atom beta to the hydroxyl group which are reacted with magnesium and a hydrogen halide to make hydrocarbon soluble product of this invention exemplified by 2,3-dimethyl-2-butanol, 2,3-dimethyl-2-pentanol, 2,3-dimethyl-3-pentanol, 2,3-dimethyl-2-hexanol, 3,4-dimethyl-4-heptanol, 2,3,4-trimethyl-3-pentanol, 3,4,4-trimethyl-3-hexanol, 1,2-dimethylcyclopentanol, 1,2,6-trimethylcyclohexanol, and the like.

Other, less preferable $C_6$–$C_{18}$ secondary and tertiary cyclic and acyclic alcohols which are reacted with magnesium and a hydrogen halide in a further embodiment of hydrocarbon soluble products of this invention are those alcohols bearing alkyl group substitution further than the beta position from the carbon atom bearing the hydroxyl group; e.g., on the gamma or delta carbons. Examples of such alcohols are 4-methyl-2-pentanol, 5-methyl-3-hexanol, 2,6-dimethyl-4-heptanol, 2-methyl-4-octanol, 3,5-dimethyl-3-hexanol, 2,6,8-trimethyl-4-nonanol, and 3-methyl-cyclohexanol.

Aromatic alcohols ($C_6$–$C_{20}$) which are reacted with magnesium in various embodiments of this invention are exemplified by phenol, benzyl alcohol, 2-tertiarybutyl phenol, alpha and beta napthol, ortho, meta, and para cresols, 1-phenylcyclohexanol, 2-phenylphenol, diphenylmethanol, 2-indanol, 2-phenylethanol, 3-phenyl-1propanol, 2,6-dimethyl phenol, iso-eugenol, 2,4,6-trimethylphenol, and the like.

Typical examples of the hydrocarbyloxy magnesium halides of this invention are ethoxymagnesium chloride, n-butoxymagnesium chloride, 2-methylpentyloxymagnesium chloride, 2-ethylhexyloxymagnesium chloride, 2-methylbutoxymagnesium chloride, n-propyloxymagnesium bromide, phenoxymagnesium chloride, etc.

The magnesium metal used in the process of this invention can be in powder, chip or granular form. Magnesium metal stored for more than 6 months or exposed to air produces blackish product containing unreacted magnesium metal. Clean freshly produced magnesium metal, but without activation with iodine, produces, while suitable, a dark-grayish product containing more than 0.1% free unreacted metal. U.S. Pat. No. 2,287,088 discloses that suitable activators for alkaline earth metals such as calcium and magnesium are aluminum, mercuric salts, iodine or anhydrous stannic chloride. Iodine is preferred in the present process as it is effective in very small amounts. Activation with iodine is conducted between about 50° to about 200° C., preferably from about 70° C. to about 120° C. in refluxing hydrocarbon solvent for 1 to 4 hours using a maximum of up to 1 gram of iodine per mole or magnesium. The amount of iodine used for activation of the magnesium is dependent on the size (exposed surface area) of magnesium metal. Fine powder about 200 sieve (75 $\mu$m) needs about 0.5 grams of iodine per mole of magnesium metal, whereas chips need about 0.2 grams of iodine per mole of magnesium metal. The magnesium metal after activation with iodine can be washed in hydrocarbon solvent before the first reaction step, but washing is not critical.

The hydrocarbon reaction medium can be any aprotic hydrocarbon that is inert to the reaction. It is preferred that the hydrocarbon solvent be aliphatic, alicyclic or aromatic and have the same or a higher boiling point than the boiling point of the oxygen containing compound. The hydrocarbon solvent used can be selected from n-hexane and n-heptane, cyclohexane, methylcyclohexane, benzene, toluene, isoparaffinic hydrocarbon fractions such as Isopar E ™, Isopar G ™ or Isopar H ™ and other commonly used inert hydrocarbon solvents. The Isopar materials are isoparaffinic solvents whose characterizing properties are set forth in Table 2 below.

Any of the hydrogen halides, dry, preferably, if anhydrous, such as hydrogen chloride, hydrogen fluoride, hydrogen iodide or hydrogen bromide can be used in practicing this invention. Anhydrous hydrogen chloride is preferred because of low cost and general availability. Mixtures of hydrogen halides can be employed, if desired. This use of low cost hydrogen halides is important in reducing processing costs and producing low cost products.

In accordance with one aspect of the present invention, there are provided stable, solid alkoxy magnesium halides. The process can use magnesium metal powder, granular magnesium or magnesium chips as the source of magnesium. The magnesium is preferably activated in an inert hydrocarbon solvent in the presence of a small amount of iodine (0.1 to 0.5 grams of iodine per mole of magnesium metal). Activation is carried out by heating the hydrocarbon solvent containing the iodine and magnesium metal, suitable, at the reflux temperature of the hydrocarbon selected, for about 60 to 120 minutes. Then in the two step version of the process an oxygen containing compound preferably an anhydrous alcohol is added to the metal with reasonably good agitation while maintaining the temperature of the reaction mixture between 50° C. and the refluxing temperature of the hydrocarbon medium. The reaction mixture is agitated, preferably at the hydrocarbon refluxing temperature, for about 2 to 4 hours to complete the reaction.

Heating is terminated and anhydrous hydrogen halide is bubbled into the reaction slurry for about thirty minutes to two hours. The reaction may be done in several stages, for example, by first adding insufficient oxygen containing compound to react with the magnesium metal. After halogenation, more oxygen containing compound is added to react with unreacted magnesium. This is followed by additional halogenation of the reaction mixture. Typically, the reaction mixture is refluxed for some time after the halogen addition is complete to ensure completion of the reaction. The anhydrous hydrogen halide is used in the range of 1.0 to 1.5 moles per mole of magnesium metal.

In the one step version of this process an appropriate selection of magnesium metal and hydrocarbon solvent are charged into a pot. If the magnesium is to be activated in situ it is done as described above. Then the oxygen containing compound is charged into the reactor and the metal slurry is brought to reflux temperature and dry hydrogen halide is introduced to the reactor under controlled conditions. Fine particle size magnesium and high boiling hydrocarbon solvents are not normally employed in the one step reaction because under these conditions the one step reaction is difficult if not impossible to control.

In accordance with another aspect of the present invention, there is provided, hydrocarbon soluble hydrocarbyloxy magnesium halides. In this aspect of the invention, the metal is reacted with a beta-alkyl substituted oxygen containing compound such as alcohols, ketones, aldehydes or esters in the range of 1.1 to 2.0 moles per mole of magnesium to form a product slurry in hydrocarbon solvent. The reaction of the magnesium metal with the oxygen containing compound can be carried out at between ambient and the reflux temperature of the hydrocarbon solvent. This slurry is then halogenated with an anhydrous hydrogen halide. The resulting soluble hydrocarbyloxy magnesium halide in a hydrocarbon solvent has more than 1 molar concentration of magnesium and RO/Mg/X molar ratio equal to about 1:1:1. A solid hydrocarbyloxy magnesium halide, such as ethoxymagnesium chloride having RO/Mg/X molar ratio of about 1:1:1, was solubilized in hydrocarbon solvent (n-heptane) by the addition of a 2-alkyl substituted oxygen containing compound such as 2-methyl-1-pentanol, or 2-ethyl-1-hexanol, in the range of 1.2 to 1.4 moles per mole of magnesium of the hydrocarbyloxy magnesium halide. The soluble product obtained had higher than one mole of magnesium concentration and an RO/Mg/X molar ratio of 1:1:1.

In accordance with a third aspect of the present invention, there are provided low melting hydrocarbyloxy magnesium halides. The hydrocarbyloxy magnesium halide is prepared as described above, but using a beta-alkyl substituted primary monohydric (normal) alcohol. Activated magnesium metal is reacted with an oxygen containing compound such as 2-methyl-1-pentanol in an amount sufficient to provide 1.3 moles of alcohol per mole of magnesium; the alcohol is added slowly while the temperature is maintained between 40° C. and 90° C. Heating is terminated and the product slurry is halogenated with an anhydrous hydrogen halide for 30 minutes to two hours to produce a hydrocarbyloxy magnesium halide product slurry. The hydrocarbyloxy magnesium halide slurry is then filtered to remove any suspended particles. The clear filtrate is then evaporated under reduced pressure at 90° C. until no further solvent is recoverable. On heating further to above 100° C., the solid mass turns into a viscous fluid but no more solvent can be recovered. On cooling, this viscous fluid turned into a hard, glassy solid. The melting range of these products were found to be between 100° and 120° C. On analysis of these products, the RO/Mg/Cl molar ratios were found to be about 1:0.8:1.2. This indicates that low melting hydrocarbyloxy magnesium halides can be produced with or without variation in the RO/Mg/Cl molar ratios.

The hydrocarbon soluble products, in yet another aspect of this invention, can be prepared by preparing a hydrocarbon insoluble hydrocarbyloxy magnesium halide using an oxygen containing compound of one to twenty carbon atoms according to the one or two step process of this invention followed by an alcohol exchange reaction with a beta-alkyl substituted secondary alcohol of five to 18 carbon atoms. Another aspect of the invention is to prepare a solid magnesium dialkoxide using a monohydric alcohol as described above in the two step process of this invention. Then an appropriate amount of a beta-alkyl substituted secondary alcohol is added to the reactor and dry hydrogen halide introduced into the reaction slurry to complete preparation of a hydrocarbon soluble hydrocarbyloxy magnesium halide.

The following examples further exemplify the invention. All examples were conducted in an inert, argon atmosphere under anhydrous conditions.

EXAMPLE 1

A round bottom three-necked reactor equipped with a reflux condenser was charged under an argon atmosphere with 8.0 grams of magnesium metal (0.329 mole), 300 ml of n-heptane, and 0.2 grams of iodine crystals. This mixture was heated to its reflux temperature (98° C.) for sixty minutes to activate the metal. Then, 21 ml (0.36m) of ethyl alcohol was added over about twenty minutes to the metal slurry at reflux temperature. The resulting reaction mixture was allowed to reflux for 120 minutes. At this point, heating was cut off and dry anhydrous hydrogen choride was bubbled into the reaction slurry. Hydrogen chloride (7.0 grams, 0.19 m) was added to the reaction slurry over abut thirty minutes. During the addition of hydrogen chloride to the reaction slurry, ethanol is released from the reaction of HCl with Mg(OEt)$_2$ to form Mg(OEt)Cl. Additional ethanol 9.0 ml, 0.155 m) was added to this slurry to complete reaction of the magnesium metal. The reaction slurry containing unreacted magnesium metal was then allowed to react with ethanol at reflux temperature for 90 to 120 minutes. The temperature of the reaction slurry was maintained between 79° C. at the temperature of the refluxing hydrocarbon. Then, heating was cut off, and the reaction slurry was reacted with dry anhydrous hydrogen chloride by slow bubbling with stirring. About 5.50 grams of hydrogen chloride (0.15M) was added over a period of about thirty minutes. Ethanol was released during the hydrogen chloride reaction and the solid reaction product turned whitish in color and fine particle in nature. Finally, the reaction slurry was allowed to reflux for thirty minutes to ensure complete reaction. The reaction slurry was filtered to collect solid product, which was dried by passing argon gas through the product and then placing it under vacuum at 65° C. Analysis of the dry powdery solvent-free ethoxy magnesium chloride showed 22.5% total magnesium, 26.8% chloride, and 49.2% $OC_2H_5$ (total base), which is a product having an RO/Mg/Cl molar ratio equal to 1.18:1.0:0.82.

EXAMPLE 2

Example 1 was repeated using 1.0 moles of Mg metal (fine powder) reacted first with 2.0 moles of ethanol followed by reaction with 1.1 moles of dry hydrogen chloride; the final product contained 22.8% Mg, 46.5% total base as $OC_2H_5$, 30.4% Cl, and no traceable metal particles.

COMPARISON EXAMPLE A

Solid Hydrocarbyloxy Magnesium Halide

A reactor equipped with a reflux condenser was charged under an argon atmosphere with 24.3 grams of magnesium metal (1 mole), 700 ml of n-heptane and 0.5 grams of iodine crystals. This mixture was heated to reflux temperature (98° C.) for 100 minutes to activate the metal. Then 93.0 grams (1 mole) of n-butyl chloride was added over about 25 minutes to this metal slurry at reflux temperature, the resulting reaction mixture was allowed to reflux for 120 minutes. Anhydrous ethyl alcohol (46 grams, re: 1 mole) was then slowly added drop-wise under good agitation. The alcohol addition was completed in one hour. The temperature of the reaction slurry was maintained between 70° C. and the temperature of the refluxing hydrocarbon. The reaction slurry was stirred at the hydrocarbon reflux temperature for 4 hours. The reaction slurry was filtered to collect solid product, which was dried under vacuum at 65° C. Analysis of the dry, powdery, solvent-free ethoxymagnesium chloride showed 22.6% total magnesium, 33% chloride and 41.3% $OC_2H_5$ (total base), which is a product having an RO/Mg/X molar ratio equal to 1:1:1.

COMPARISON EXAMPLE B $Mg(OEt)_2$ granular (51.0 grams) was added under argon to a reactor flask along with 300 ml of n-heptane. The slurry was heated up to 80° C. with stirring and under argon atmosphere. The analysis of $Mg(OEt)_2$ showed 21.68% total Mg and 76.2% total base as $—OC_2H_5$.

To this slurry 15.0 grams of dry anhydrous hydrogen chloride was bubbled slowly under agitation over a period of about sixty minutes. During the addition of hydrogen chloride, release of free ethanol was seen; but after some time not much free ethanol was found; and the product in the slurry was filtered and the solid product was dried under vacuum at 55° C. for two hours, then the dried product was analyzed and found to contain 18.16% total magnesium, 47.34% total base as $OC_2H_5$, 15.95% Cl, and 18.52% ethanol (bound).

EXAMPLES 3 TO 8

Several experiments were carried out to prepare a hydrocarbon soluble hydrocarbyloxy magnesium chloride by using dry anhydrous hydrogen chloride.

In this aspect of the invention, three qualitative tests were carried out to verify if soluble hydrocarbyloxy magnesium chloride can be made by reacting a solid hydrocarbyloxy magnesium chloride, such as EtOMgCl, BuOMgCl, PhOMgCl, made by the process of this invention, with 2-alkyl-substituted alcohols such as 2-methyl-1-pentanol and 2-ethyl-1-hexanol.

Examples 3 to 8 Procedure 10.0 grams each of EtOMgCl (0.092 m), BuOMgCl (0.074 m) and PhOMgCl (0.06 m) were slurried separately in three bottles in 100 ml of n-heptane. Added to each was 20 ml (0.16 m) of 2-methyl-1-pentanol. The samples were kept in a heating bath at 55° C. with occasional shaking. Reaction was seen within a few minutes, and most of the solids were dissolved in less than one hour. All three products were filtered to remove some suspended solid particles from the solution products. Soluble product filtrates were analyzed for total Mg and found to contain more than 95% of the magnesium added as starting material.* Results are shown in the following Table I. In the same manner, these three solid alkoxides were made soluble using 2-ethyl hexanol. The results of Examples 3 to 8 are set forth in Table I.

TABLE I

| Hydrocarbon Soluble Hydrocarbyloxy Magnesium Chlorides | | |
|---|---|---|
| | Alcohols (1.3 M to 2.0 Mole/Mole of Mg) | |
| Start Material | 2-Methyl-1-Pentanol | 2 Ethyl-1-Hexanol |
| EtOMgCl* + n-heptane | Soluble (0.76 M) | Soluble (0.7 M) |
| BuOMgCl* + n-heptane | Soluble (0.60 M) | Soluble (0.7 M) |
| PhOMgCl* + n-heptane | Soluble (0.50 M) | Soluble (0.7 M) |

*All the solid alkoxymagnesium halides used were made by the process of Example 1.

These examples demonstrate that hydrocarbon soluble hydrocarbyloxy magnesium chlorides can be made from solid hydrocarbon insoluble hydrocarbyloxy magnesium chlorides (made by HCl route such as EtOMgCl, BuOMgCl, PhOMgCl) by reacting with more than one mole, preferably 1.3 to 1.5 moles of 2-alkyl-substituted alcohols, such as 2-methyl-1-pentanol, 2-ethyl-1-hexanol in n-heptane at temperatures between ambient and 100° C.

EXAMPLE 9

A reactor equipped with a reflux condenser was charged under an argon atmosphere with 5.0 grams (0.206 m) magnesium metal powder, 200 ml of Isopar E isoparaffinic hydrocarbon solvent, and a few crystals (0.15 gram) of iodine. This mixture was heated to reflux temperature (121° C.) for about sixty minutes to activate the metal. Anhydrous phenol crystals (28 grams, 0.298 m), along with 50 ml of Isopar E, was taken in an addition funnel and kept warm to about 50° C. by heating strips to make sure that all phenol crystals were melted in Isopar E solvent before being added to the metal slurry. Phenol (melted) in Isopar E was added to the metal slurry over twenty minutes. Reaction between phenol and metal occurred at reflux temperature after about ten to fifteen minutes. Phenol-Mg metal reaction was continued at reflux temperature (120°–121° C.) for about two hours. Then, heating was ended and 4.0 grams (0.109 m) dry anhydrous hydrogen chloride was bubbled slowly into the phenol-magnesium reaction product mixture with good agitation at 70° C. The product (solid) was a grayish fine solid. After hydrogen chloride addition was completed, the slurry was heated up and a crystalline type solid obtained at 95° C. and above. The slurry was allowed to react for another two hours to complete the reaction between the remaining magnesium metal and phenol. The slurry was then cooled to 60° C. and 5.0 grams (0.137 m) of dry anhydrous hydrogen chloride was added by bubbling it slowly into the reaction mixture. The reaction slurry became thick and the product was whitish-gray in color. The reaction slurry was heated to 100° C. for one hour and the thick slurry containing fine particles turned into coarse round solids. The slurry was filtered while it was hot to collect a solid product which was washed with warm Isopar E solvent to remove entrained, excess phenol. The solid was dried by passing argon gas through the product overnight. The solid product and filtrates were analyzed.

The filtrate was tested as usual for Mg content and none was found. The filtrate on cooling to room temperature generated phenol crystals, which indicates that the filtrate containing Isopar E and phenol could be recycled in the subsequent reaction. Analysis of the solid whitish-gray product showed 14.54% total magnesium, 57.13% total base as $-OC_6H_5$, 20.6% Cl, and the remainder was Isopar E. The solid product had an RO/Mg/X (i.e., $C_6H_5O/Mg/Cl$) molar ratio almost equal to 1:1:1. Samples of phenoxymagnesium chlorides made by both methods (H.C. and A.C.) were analyzed by C-13 NMR spectra.

COMPARISON EXAMPLE C

A reactor equipped with a reflux condenser was charged under an argon atmosphere with 6.55 gm of magnesium metal powder (0.269 moles), 250 ml of Isopar E isoparaffinic hydrocarbon solvent and a few crystals (0.2 gm) of iodine. This mixture was heated to reflux temperature (121° C.) for about 60 minutes to activate the metal. Then, 28.0 ml (0.27 moles) of n-butyl chloride was added in 30 minutes to this metal slurry at reflux temperature; the resulting reaction mixture was allowed to reflux for 90 minutes. Anhydrous crystalline phenol ($C_6H_5OH$) 28 gm (0.298 moles) was then added slowly in melted form along with Isopar E solvent (50° C.) under good agitation. The phenol addition was completed in 20 minutes. During addition of phenol, heating was cut off and maintained at the reflux with release of butane from the reaction. The reaction slurry turned from a grayish to a whitish color. The reaction slurry was then heated up to 90° C. with distillation of the refluxing butane. The slurry color turned from gray to white with no visible metal particles. Reaction was continued at 90° C. for another two hours with the addition of another 12 gms (0.128 moles) of phenol. The second addition of phenol was to determine if any magnesium solubilized. The reaction slurry was then filtered to collect solid product. The solid product was washed with pentane to remove leftover solvents. The filtrate was tested for magnesium and found to be nil. The solid was dried under argon pressure until it was found to be a free flowing powder. Analysis of the solid white product showed 14.82% total magnesium, 56.78% $C_6H_5O$, 21.27% Cl, and remaining is free solvent. The filtrate was found to have all the excess phenol in it. This solid white product had an RO/Mg/X (i.e., $C_6H_5O/Mg/Cl$) molar ratio almost equal to 1:1:1.

EXAMPLE 10

Following the procedure of Example 1, 24.31 grams of magnesium metal powder (1.0 moles) in about one liter of n-heptane was activated with 0.6 gram iodine for about sixty minutes at reflux temperature. This activated magnesium metal was then reacted with 137 ml of n-butyl alcohol (1.5 m) at reflux temperature for three hours, which included the time of addition of the alcohol. After three hours of alcohol-metal reaction, the heating was cut off and 28.0 grams (0.77 m) of anhydrous hydrogen chloride was bubbled into the reaction mixture with agitation over ninety minutes. Then, the slurry was allowed to react at reflux temperature for about ninety minutes until all remaining unreacted metal reacted and released butanol. Finally, heating was cut off and 12.0 grams (0.33 m) of dry anhydrous hydrogen chloride was bubbled into the slurry under good agitation over sixty minutes. Finally, the slurry was allowed to react for another sixty minutes and then filtered. The filtration was fast, and the solid product obtained on filtration was dried at 70° C. under reduced pressure. The dried product was a light, fine, grayish-white powder. On analysis, the final dried product contained 17.90% Mg, 53.40% total base as $OC_4H_9$ and 26.2% Cl.

The prior art has recognized that when an alkylhalide (RCl) is reacted with magnesium metal and a primary alcohol (R'OH) the compounds formed can include $Mg(OR')_2$ Mg Hal, Hal Mg OR, $Mg(OR')_2$, ROH+Mg Hal$_2$, etc. Unfortunately most workers in the field were only interested in further reacting such reaction products with a transition metal halide, frequently titanium tetrachloride, to make a polymerization catalyst so they never bothered to isolate and/or identify the intermediate organometallic product. Turova et al., cited above, noted this lack of reported physical and chemical characteristics of these intermediates in the art.

The compounds of the present process and products of comparison examples have been studied and identified by carbon-13 nuclear magnetic resonance using cross polarization and magic angle spinning [C-13 NMR (Cp/MAS)] spectra in order to provide chemical identification of the products of the invention. These spectroscopic studies included spectra of $Mg(OC_2H_5)_2$, a commercial product obtained from Dynamit-Noble Company, the $Mg(OC_2H_5)Cl$ compound of Comparison Example A and the products of Examples 1, 9 and Comparison Example C.

The drawings are C-13 NMR (CP/MAS) spectra of products of the process of this invention and comparisons with products of other processes or known compounds.

The C-13 NMR (CP/MAS) spectra of magnesium ethoxide, ethoxymagnesium chloride product of Comparison Example A and the ethoxymagnesium chloride of Example 1 were determined and set forth in FIG. 1. These spectra, Example A and the spectra of ethoxymagnesium chloride of Example 1 were determined and set forth in FIG. 1. These spectra are compared in Table II below. As can be seen in FIG. 1 and Table II, the product of the alkyl chloride process of Comparison Example A [EtOMgCl (A.C. Method)] and the product of Example 1 [EtOMgCl (H.C. Method)] are significantly different but do not appear to contain a discreet or significant amount of magnesium ethoxide (MgOEt$_2$). A comparison of the major and minor absorption of the two differently produced MgOEtCl products indicate that neither product contains ethoxide species of a similar nature. The ethoxymagnesium chloride of Example 1 shows some indication of an ethoxide component whose respective absorptions occur at 58.6 and 22.2 ppm. Since the difference between peaks is 36.4 ppm, which is approximately the same as for magnesium ethoxide, the product of Example 1 may contain some amount of magnesium ethoxide.

TABLE II

Comparison of C-13 NMR Absorption (in ppm) of Mg(OEt)$_2$ and Samples of EtOMgCl

| Mg(OEt)$_2$ | Comparison Example A EtOMgCl | Example 1 EtOMgCl | |
|---|---|---|---|
| — | — | 63.8 | |
| — | 62.3 | — | |
| — | 59.6 | 60.7 | |
| — | 58.1 | 58.6 | |
| 57.4 | — | — | |
| — | — | 52.6 | 36.4 ppm |
| — | 36.7 ppm | — | |
| — | — | 32.5 | |
| — | — | 29.0 | |
| — | 22.3 | 22.2 | |
| 20.7 | 20.8 | — | |
| — | 19.7 | 19.85 | |
| — | 18.5 | 18.5 | |
| — | 17.3 | — | |

Figure 2:
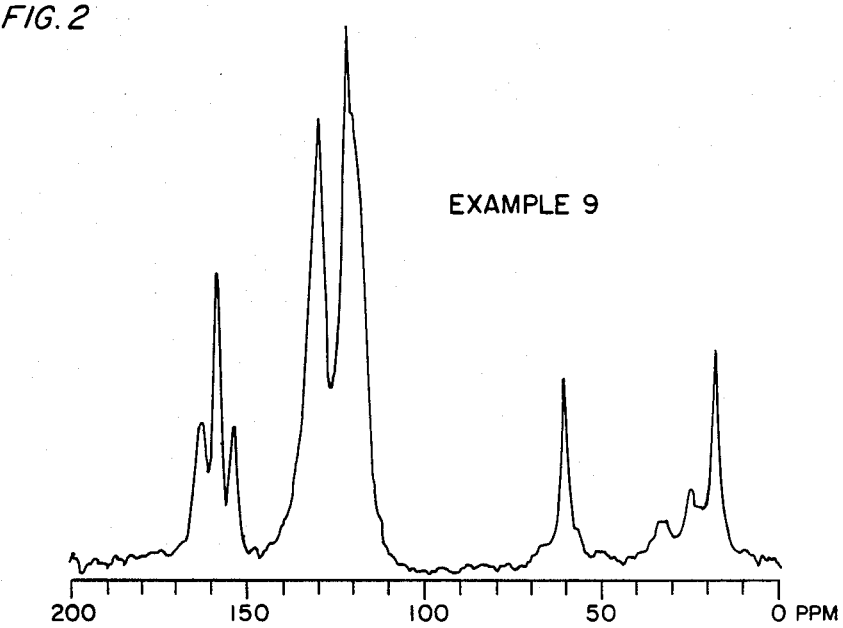
Figure 2:
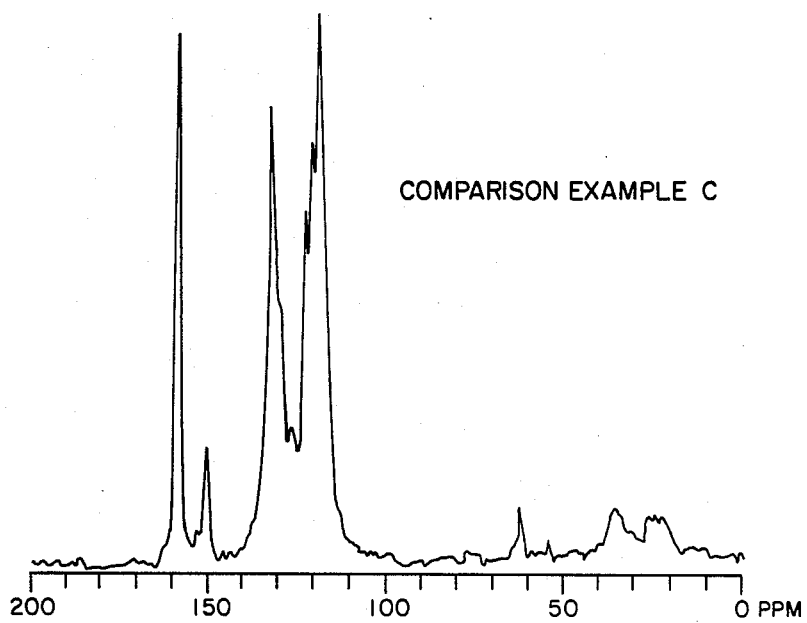

The C-13 NMR (CP/MAS) spectra of Comparison Example C and Example 9 set forth in FIG. 2 indicate the samples are different from each other. The spectra of Example 9 surprisingly shows some prominent ethyl peaks at 60.30 and 18.0 ppm that the spectra of Comparison Example C does not exhibit. The two peaks to the left in the Example 9 spectra are spinning sidebands from the phenyl peaks. The spectra of Comparison Example C at two spinning rates shows clearly that there are no Sp 3 carbon peaks in the spectrum. Although the spectra of Example 10 and Comparison Example A are distinct, it would not be justified to conclude that they share no common chemical component. It is possible to conclude that there could be a small amount of Comparison Example C like the solid product in Example 9. The limit is defined by the intensity in the Example 9 spectra at 150.1 ppm, on the shoulder of the peak at 153.6 ppm, or by its intensity at 131.5 ppm, on the left shoulder of the peak centered at 129.6 ppm, or by the intensity at 118.4 ppm on the right side of the peak at 120.2 ppm. In none of these cases is the intensity zero. Table III shows a comparison of absorptions in ppm.

TABLE III

Comparison of C-13 NMR Absorption (in ppm) of Phenoxide (Calculated) and PhOMgCl Samples

| PhO- (Calculated) | Example 9 PhOMgCl | Comparison Example C PhOMgCl |
|---|---|---|
| 168.1 | 162.9 | — |
| | 158.3 | 158.3 |
| | 153.6 | — |
| | — | 150.1 |
| 130.4 | — | 131.5 |
| | 129.6 | 129.4 |
| | — | 125.8 |
| | 122.1 | 121.8 |
| 120.3 | 120.2 | 120.1 |

TABLE III-continued

Comparison of C-13 NMR Absorption (in ppm) of Phenoxide (Calculated) and PhOMgCl Samples

| PhO- (Calculated) | Example 9 PhOMgCl | Comparison Example C PhOMgCl |
|---|---|---|
| | — | 118.4 |
| 114.9 | 60.30 | — |
| | — | — |
| | 18.0 | — |

What is claimed is:

1. A process for producing a hydrocarbyloxy magnesium halide of the formula ROMgX, wherein RO is a hydrocarbyloxy group having 1 to 20 carbon atoms and X is a halide, comprising reacting magnesium metal with an oxygen containing compound containing 1 to 20 carbon atoms and an anhydrous hydrogen halide under anhydrous conditions, in an inert atmosphere and in a hydrocarbon reaction medium.

2. The process of claim 1 in which the magnesium metal is activated before reacting it with the oxygen containing compound and the anhydrous hydrogen halide.

3. The process of claim 1 in which the magnesium metal is activated by refluxing it in a hydrocarbon solvent with an activating amount of iodine.

4. The process of claim 1 in which the reaction is carried out between 40° C. and 200° C.

5. The process of claim 1 in which the oxygen containing compound is selected from monohydric alkanols, cycloalkanols and aromatic alcohols having 6 to 18 carbon atoms.

6. The process of claim 1 in which the hydrocarbon reaction medium is a hydrocarbon solvent selected from n-hexane, n-heptane, cyclohexane, methylcyclohexane, benzene, toluene and isoparaffinic hydrocarbon fractions boiling at 200° C. or less.

7. The process of claim 1 in which the oxygen containing compound is selected from beta-alkyl substituted primary monohydric alcohol containing 5 to 18 carbon atoms, beta-alkyl substituted secondary alcohols containing 5 to 18 carbon atoms and beta-alkyl substituted cyclic and acyclic tertiary alcohols containing 6 to 18 carbon atoms.

8. The process of claim 1 in which the inert atmosphere is selected from argon and nitrogen.

9. The process of claim 1 in which the anhydrous hydrogen halide is anhydrous hydrogen chloride.

10. The process of claim 1 in which the reaction is conducted in a hydrocarbon reaction medium having a boiling point above 100° C. and a fine particle size activated magnesium is first reacted with an oxygen containing compound to form a reaction produce which is reacted with dry hydrogen chloride.

11. The process of claim 7 in which the beta-alkyl substituted alcohol selected is used in the range of 1.1 to 2.0 moles of alcohol per mole of magnesium.

12. A process for producing a hydrocarbon soluble hydrocarbyloxymagnesium halide of the formula ROMgX wherein RO is a hydrocarbyloxy group having 5 to 18 carbon atoms and X is a halide comprising reacting a hydrocarbon insoluble magnesium dialkoxide of the formula Mg(OR')$_2$ wherein OR' is a primary alkoxy group containing 1 to 20 carbon atoms with a dry hydrogen halide and a beta-alkyl substituted secondary alcohol containing 5 to 18 carbon atoms to produce the hydrocarbon soluble hydrocarbyloxymagnesium halide of the formula ROMgX.

13. The process of claim 5 wherein the oxygen containing compound selected is a monohydric alcohol of 1 to 20 carbon atoms which is reacted in the presence of a dry hydrogen halide with magnesium metal to produce a hydrocarbon insoluble hydrocarbyloxymagnesium halide which is reacted with a betaalkyl substituted secondary alcohol to effect an alcohol exchange and produce a hydrocarbon soluble hydrocarbyloxymagnesium halide.

14. A process for producing a hydrocarbon soluble hydrocarbyloxymagneisum halide of the formula ROMgX wherein RO is a hydrocarbyloxy group having 5 to 18 carbon atoms and X is a halide comprising reacting a hydrocarbon insoluble hydrocarbyloxymagnesium halide of the formula R'OMgX wherein R'O is a primary alkoxy group containing 1 to 20 carbon atoms with a dry hydrogen halide and a beta-alkyl substituted secondary alcohol containing 5 to 18 carbon atoms to produce the hydrocarbon soluble hydrocarbyloxymagnesium halide of the formula ROMgX.

15. The process of claim 3, 4, 5, 6, 7, 8, 11, 12, 13 or 14 wherein the hydrogen halide is hydrogen chloride.

* * * * *